(12) United States Patent
Nieten et al.

(10) Patent No.: US 9,588,053 B2
(45) Date of Patent: Mar. 7, 2017

(54) REPLACEMENT INDICATOR, ELASTOMERIC ARTICLES AND METHODS

(71) Applicant: Firestone Industrial Products Company, LLC, Indianapolis, IN (US)

(72) Inventors: Jason D. Nieten, Noblesville, IN (US); Graham R. Brookes, Noblesville, IN (US); Michael C. Howard, Noblesville, IN (US); Pradipta N. Moulik, Carmel, IN (US)

(73) Assignee: Firestone Industrial Products Company, LLC, Indianapolis, IN (US)

( * ) Notice: Subject to any disclaimer, the term of this patent is extended or adjusted under 35 U.S.C. 154(b) by 69 days.

(21) Appl. No.: 14/379,668

(22) PCT Filed: Feb. 28, 2013

(86) PCT No.: PCT/US2013/028245
§ 371 (c)(1),
(2) Date: Aug. 19, 2014

(87) PCT Pub. No.: WO2013/130755
PCT Pub. Date: Sep. 6, 2013

(65) Prior Publication Data
US 2015/0000589 A1  Jan. 1, 2015

Related U.S. Application Data

(60) Provisional application No. 61/604,760, filed on Feb. 29, 2012.

(51) Int. Cl.
*G01N 21/78* (2006.01)
*B60C 23/20* (2006.01)
(Continued)

(52) U.S. Cl.
CPC ............. *G01N 21/78* (2013.01); *B60C 23/20* (2013.01); *B60G 11/27* (2013.01); *F16F 9/0454* (2013.01);
(Continued)

(58) Field of Classification Search
CPC ........... G01N 21/78; G01N 2021/7796; G01N 21/29; B60C 23/20; F16F 9/3264;
(Continued)

(56) References Cited

U.S. PATENT DOCUMENTS 3,739,662 A    6/1973  Windelman
4,595,312 A *  6/1986  Corless ................... E01F 9/073
                                                116/63 R
(Continued)

FOREIGN PATENT DOCUMENTS

JP    2000 075794    3/2000
JP    2000 221884    8/2000
(Continued)

OTHER PUBLICATIONS

International Search Report for corresponding patent application No. PCT/US2013/028245 dated May 31, 2013.

*Primary Examiner* — R. A. Smith
*Assistant Examiner* — Tania Courson
(74) *Attorney, Agent, or Firm* — Thomas R. Kingsbury; Fay Sharpe LLP

(57) ABSTRACT

A replacement indicator can be operatively associated with an elastomeric article such that the replacement indicator is visually observable. In some cases, the replacement indicator can be secured on or along the elastomeric article. Gas spring assemblies and pneumatic tires including a replacement indicator, as well as methods of manufacture are also included.

20 Claims, 11 Drawing Sheets

(51) Int. Cl.
  *B60G 11/27* (2006.01)
  *F16F 9/32* (2006.01)
  *F16F 9/04* (2006.01)
  *G01K 3/04* (2006.01)
  *G01N 21/29* (2006.01)
  *G01N 21/77* (2006.01)

(52) U.S. Cl.
  CPC .............. *F16F 9/3264* (2013.01); *G01K 3/04* (2013.01); *G01N 21/29* (2013.01); *B60G 2202/152* (2013.01); *B60G 2204/111* (2013.01); *B60G 2206/90* (2013.01); *F16F 2230/24* (2013.01); *G01N 2021/7796* (2013.01); *Y10T 29/49826* (2015.01)

(58) Field of Classification Search
  CPC ................ F16F 9/0454; F16F 2230/24; B60G 2202/152; B60G 2206/90; B60G 11/27; B60G 2204/111; G01K 3/04; Y10T 29/49826
  USPC ............................. 116/201, 207, 208; 29/428
  See application file for complete search history.

(56) References Cited

U.S. PATENT DOCUMENTS

| | | | |
|---|---|---|---|
| 5,349,718 A | 9/1994 | Gibbon | |
| 5,630,372 A * | 5/1997 | Ramsey | C12Q 1/26 116/206 |
| 5,797,344 A * | 8/1998 | Ramsey | G01N 31/229 116/206 |
| 5,824,397 A | 10/1998 | Koops et al. | |
| 6,047,436 A * | 4/2000 | Rohrbach | B60S 1/38 15/250.001 |
| 6,544,925 B1 | 4/2003 | Prusik | |
| 6,775,877 B1 * | 8/2004 | Broszniowski | B60S 1/3801 116/200 |
| 7,153,381 B2 * | 12/2006 | Majumdar | G09F 3/04 152/525 |
| 7,185,601 B2 * | 3/2007 | Carpenter | G01N 21/293 116/206 |
| 7,338,914 B2 * | 3/2008 | Conwell | B32B 7/12 428/343 |
| 7,364,210 B2 * | 4/2008 | Schainholz | A61L 2/28 116/207 |
| 2002/0066507 A1 * | 6/2002 | Sievi-Korte | B60C 1/0016 152/209.16 |
| 2002/0083883 A1 * | 7/2002 | Inoue | G01N 31/223 116/206 |
| 2006/0042366 A1 * | 3/2006 | Carrus | B60C 23/20 73/146 |
| 2007/0257833 A1 | 11/2007 | Nordmeyer | |
| 2013/0068155 A1 * | 3/2013 | Patel | G01K 3/04 116/201 |

FOREIGN PATENT DOCUMENTS

| | | |
|---|---|---|
| JP | 2009 137549 | 6/2009 |
| KR | 20110052334 | 5/2011 |
| WO | WO 2006/068999 | 6/2006 |

* cited by examiner

REPLACEMENT INDICATOR, ELASTOMERIC ARTICLES AND METHODS

This application is the National Stage of International Application No. PCT/US2013/028245, filed on Feb. 28, 2013, which claims the benefit of priority from U.S. Provisional Patent Application No. 61/604,760, filed on Feb. 29, 2012, the subject matter of which is hereby incorporated herein by reference in its entirety.

BACKGROUND

The subject matter of the present disclosure broadly relates to the art of elastomeric articles and, more particularly, to a replacement indicator for elastomeric articles as well as elastomeric articles (e.g., gas spring assemblies and pneumatic tires) that include a replacement indicator and methods of manufacturing the same.

The subject matter of the present disclosure may find particular application and use in conjunction with components for wheeled vehicles, and will be shown and described herein with reference thereto. However, it is to be appreciated that the subject matter of the present disclosure is also amenable to use in other applications and environments, and that the specific uses shown and described herein are merely exemplary. For example, the subject matter of the present disclosure could be used in connection with non-wheeled vehicles, elastomeric components for support structures, height adjusting systems and actuators associated with industrial machinery, components thereof and/or other such equipment. Accordingly, the subject matter of the present disclosure is not intended to be limited to use associated with elastomeric components of wheeled vehicles.

Wheeled motor vehicles of most types and kinds include a sprung mass, such as a body or chassis, for example, and an unsprung mass, such as two or more axles or other wheel-engaging members, for example, with a suspension system disposed therebetween. Typically, a suspension system will include a plurality of spring devices as well as a plurality of damping devices that together permit the sprung and unsprung masses of the vehicle to move in a somewhat controlled manner relative to one another. Movement of the sprung and unsprung masses toward one another is normally referred to in the art as jounce motion while movement of the sprung and unsprung masses away from one another is commonly referred to in the art as rebound motion.

Known gas suspension systems, such as for use on vehicles, for example, normally include one or more gas spring assemblies that utilize a flexible sleeve or bellows that is formed from elastomeric material. In many cases, the flexible sleeve or bellows will be formed from one or more layers or plies of elastomeric material (e.g., rubber) with one or more layers or plies of reinforcing material embedded therein. Regardless of the construction, however, the flexible sleeve or bellows at least partially defines a spring chamber that contains pressurized gas and permits the gas spring assemblies to support a load.

As a result of the relative movement between the sprung and unsprung masses of a vehicle, gas spring assemblies are routinely displaced between extended and compressed conditions, which results in repeated bending and unbending of the flexible sleeve or bellows. Furthermore, known gas suspension systems typically provide the capability of adjusting the height and/or alignment (i.e., leveling) of a sprung mass (e.g., a body or chassis of a vehicle) relative to an unsprung mass thereof (e.g., a wheel-engaging member or axle housing of the vehicle). Such actions can result in additional bending and unbending of the flexible sleeve or bellows of the gas spring assemblies.

Elastomeric devices, such as flexible sleeves and bellows, for example, may, under some conditions, experience a decrease in performance and/or other characteristics as a result of such cyclical flexing (i.e., bending and unbending) and/or as a result of exposure to certain environmental conditions and/or agents, or as a result of a combination of these factors. As such, it may be desirable, in some cases, to identify and/or assist in predicting the occurrence of such decreases in performance and/or other characteristics, whether presenting suddenly or gradually over an extended duration.

Environmental agents, such as have been referenced above, can include chemical agents (e.g., oxygen ($O_2$), ozone ($O_3$), volatile organic compounds, etc.) and/or physical agents (e.g., heat, such as may disadvantageously increase the rate of oxygen ($O_2$) degradation). Ozone, in particular, has been identified as contributing to performance loss in elastomeric articles. In some cases, cumulative exposure to ozone, particularly when occurring over a prolonged duration, can contribute to the degradation of many rubber compounds. Since performance loss due to ozone exposure is typically a slow process, any performance loss may not be visually identifiable in some elastomeric articles until after the useful lifetime of the elastomeric article has expired.

Accordingly, it is believed desirable to develop a replacement indicator for elastomeric articles, as well as elastomeric articles that include such replacement indicators and methods of manufacturing the same.

BRIEF SUMMARY

One example of a replacement indicator in accordance with the subject matter of the present disclosure for use in cooperation with an associated elastomeric article can include a material in which a visual characteristic of at least a portion of the material will change from a first visually-apparent condition to a second visually-apparent condition that is different from the first visually-apparent condition upon exposure of the replacement indicator to a predetermined level of one or more environmental agents with the change from the first condition to the second condition capable of bearing a relation to a material characteristic of the associated elastomeric article.

One example of an assembly in accordance with the subject matter of the present disclosure can include an elastomeric article and a replacement indicator operatively associated with the elastomeric article. The replacement indicator can include a material having a visual characteristic that changes from a first visually-apparent condition to a second visually-apparent condition that is different from the first visually-apparent condition upon exposure to a common, predetermined level of one or more environmental agents with the change from the first condition to the second condition correlating to a change in a material characteristic of the elastomeric article.

One example of a method of manufacturing an assembly in accordance with the subject matter of the present disclosure can include providing a replacement indicator that includes a material capable of changing a visually-observable characteristic from a first condition to a second condition upon exposure to a predetermined level of one or more environmental agents. The method also includes providing an elastomeric article, and supporting the replacement indicator on or adjacent the elastomeric article such that exposure to one or more environmental agents is approximately equal for the replacement indicator and the elastomeric article. In some cases, supporting the replacement indicator on the elastomeric article can include securing the replacement indicator to an exterior surface of the elastomeric article.

One example of a method of monitoring a characteristic of an elastomeric article in accordance with the subject matter of the present disclosure can include providing an elastomeric article to be monitored. The method can also include providing a replacement indicator that includes a material capable of changing a visually-observable characteristic upon exposure to a predetermined level of one or more environmental agents. The method can further include correlating one or more visually-observable characteristics of the material with one or more corresponding material characteristics of the elastomeric article, such that a material characteristic of the elastomeric article can be identified by the change in the visually-observable characteristic of the replacement indicator upon exposure of the replacement indicator and the elastomeric article to a common, predetermined level of the one or more environmental agents.

In some cases, the elastomeric article can include one of an elastomeric sleeve for a gas spring assembly, an elastomeric spring bellows for a gas spring assembly, and a pneumatic tire.

One example of a gas spring assembly in accordance with the subject matter of the present disclosure can include a flexible wall extending circumferentially about a longitudinally-extending axis between opposing first and second ends. A first end member can be secured across the first end of the flexible wall, and a second end member can be secured across the second end of the flexible wall such that a spring chamber is at least partially defined by the flexible wall between the first and second end members. A replacement indicator can be secured on one of the flexible wall, the first end member and the second end member. The replacement indicator can include a material having a visual characteristic that changes from a first condition to a second condition upon exposure to a predetermined level of one or more environmental agents with the change from the first condition to the second condition correlating to a change in a material characteristic of the flexible wall.

One example of a pneumatic tire in accordance with the subject matter of the present disclosure can include a pneumatic tire body and a replacement indicator. The pneumatic tire body can include a tread portion, at least one bead portion an at least one side wall portion extending between and interconnecting the tread portion and the at least one bead portion. The replacement indicator can be secured on or along the at least one side wall portion and can include a material having a visual characteristic that changes from a first condition to a second condition upon exposure to a predetermined level of one or more environmental agents with the change from the first condition to the second condition correlating to a change in a material characteristic of the pneumatic tire body.

In some cases, the predetermined level of one or more environmental agents can be a predetermined, cumulative level of exposure occurring over an extended period of time, such as a period of time within a range of from approximately one month to approximately 72 months, for example.

DETAILED DESCRIPTION

Figure 1:
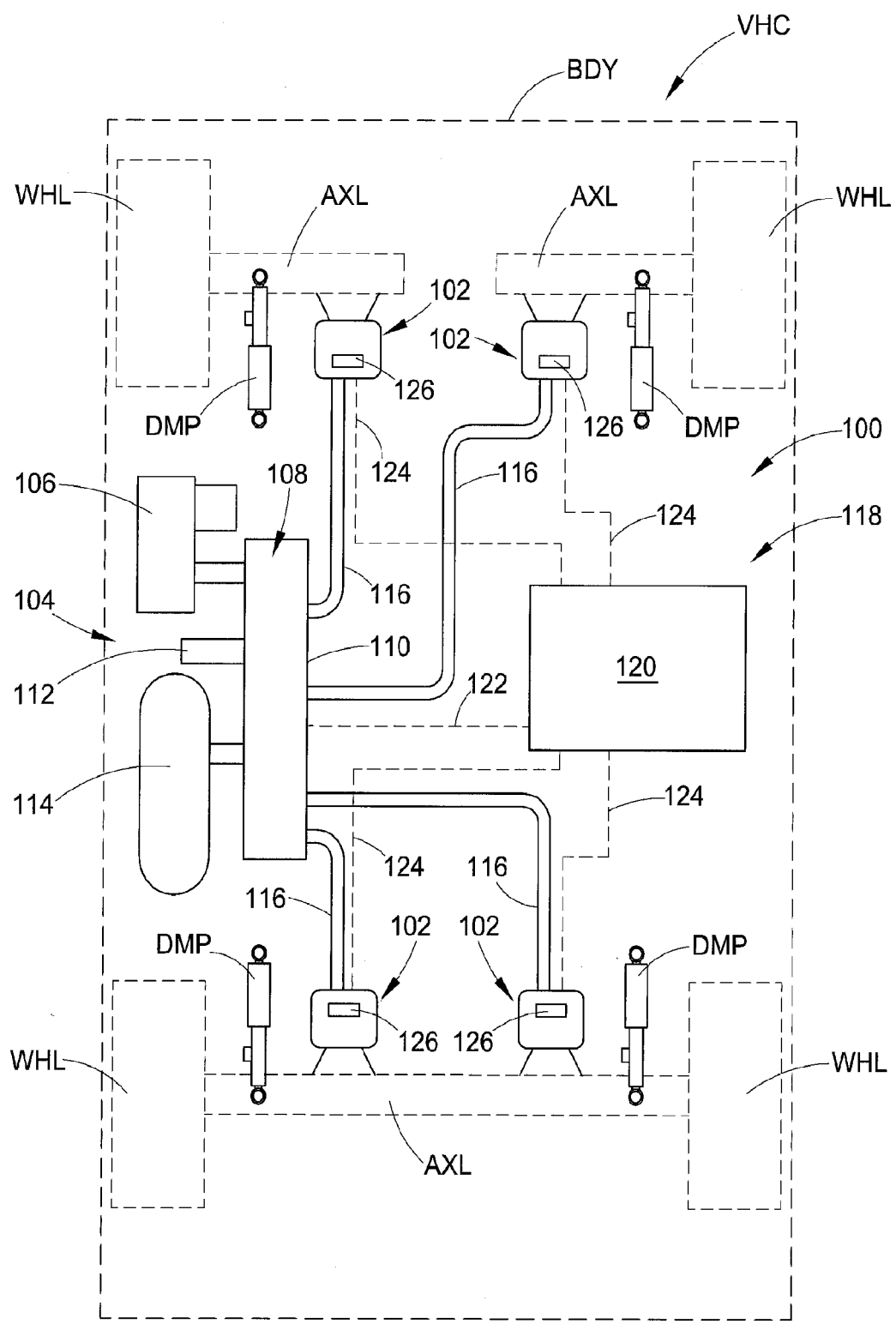
FIG. 1 is a schematic representation of one example of a suspension system of an associated vehicle including gas spring assemblies in accordance with the subject matter of the present disclosure.

Turning now to the drawings, wherein the showings are for the purpose of illustrating exemplary embodiments of the present novel concept and not for the purpose of limiting the same, FIG. 1 illustrates one embodiment of a suspension system 100 disposed between a sprung mass, such as an associated vehicle body BDY, for example, and an unsprung mass, such as an associated wheel WHL or an associated axle AXL, for example, of an associated vehicle VHC. It will be appreciated that any one or more of the components of the suspension system can be operatively connected between the sprung and unsprung masses of the associated vehicle in any suitable manner. Additionally, it will also be appreciated that such a suspension system of the vehicle can also optionally include a plurality of damping members, such as dampers DMP, for example, and that any such damping members can also be operatively connected between the sprung and unsprung masses of the associated vehicle in any suitable manner.

The suspension system can also include a plurality of gas spring assemblies supported between the sprung and unsprung masses of the associated vehicle. In the embodiment shown in FIG. 1, suspension system 100 includes four gas spring assemblies 102, one of which is disposed toward each corner of the associated vehicle adjacent a corresponding wheel WHL. However, it will be appreciated that any other suitable number of gas spring assemblies could alternately be used in any other configuration or arrangement. As shown in FIG. 1, gas spring assemblies 102 are supported between axles AXL and body BDY of associated vehicle VHC. Additionally, it will be recognized that the gas spring assemblies shown and described in FIG. 1 (e.g., gas spring assemblies 102) are of a rolling-lobe type construction. It is to be understood, however, that gas spring assemblies of any other type, kind and/or construction could alternately be used.

Suspension system 100 also includes a pressurized gas system 104 operatively associated with the gas spring assemblies for selectively supplying pressurized gas (e.g., air) thereto and selectively transferring pressurized gas therefrom. In the exemplary embodiment shown in FIG. 1, pressurized gas system 104 includes a pressurized gas source, such as a compressor 106, for example, for generating pressurized air or other gases. A control device, such as a valve assembly 108, for example, is shown as being in communication with compressor 106 and can be of any suitable configuration or arrangement. In the exemplary embodiment shown, valve assembly 108 includes a valve block 110 with a plurality of valves (not shown) supported thereon. Valve assembly 108 can also optionally include a suitable exhaust, such as a muffler 112, for example, for venting pressurized gas from the system. Optionally, pressurized gas system 104 can also include a reservoir 114 in fluid communication with valve assembly 108 and suitable for storing pressurized gas.

Valve assembly 108 is in communication with gas spring assemblies 102 through suitable gas transmission lines 116. As such, pressurized gas can be selectively transferred into and/or out of the gas spring assemblies through valve assembly 108, such as to alter or maintain vehicle height at one or more corners of the vehicle, for example.

Suspension system 100 also includes a control system 118 capable of communication with any one or more other systems and/or components (not shown) of suspension system 100 for selective operation and/or control thereof. Control system 118 includes a controller or electronic control unit (ECU) 120 in communication with compressor 106 and/or valve assembly 108, such as through a conductor or lead 122, for example, for selective operation and control thereof, including supplying and exhausting pressurized gas to and/or from gas spring assemblies 102. Controller 120 can be of any suitable type, kind and/or configuration.

Control system 118 can also, optionally, include one or more height (or distance) sensing devices (not shown in FIG. 1), such as, for example, may be operatively associated with the gas spring assemblies and capable of outputting or otherwise generating data, signals or other communications having a relation to a height of the gas spring assemblies or a distance between other components of the vehicle. Such height sensing devices can be in communication with ECU 120, which receives the height or distance signals therefrom. The height sensing devices can be in communication with ECU 120 in any suitable manner, such as through conductors or leads 124, for example. Additionally, it will be appreciated that the height sensing devices can be of any suitable type, kind or construction without departing from the scope and intent of the present novel concept.

Additionally, an assembly in accordance with the subject matter of the present disclosure can include an elastomeric article and a replacement indicator operatively associated with the elastomeric article and capable of providing a visual indication of the exposure of the elastomeric article to a predetermined level of one or more environmental agents. As one example of such an assembly, one or more gas spring assemblies can include a replacement indicator operatively associated therewith. In the exemplary arrangement in FIG. 1, gas spring assemblies 102 are shown as including a replacement indicator 126 secured to a portion of a gas spring assembly. It will be appreciated, however, that other arrangements and/or configurations could alternately be used.

Figure 2:
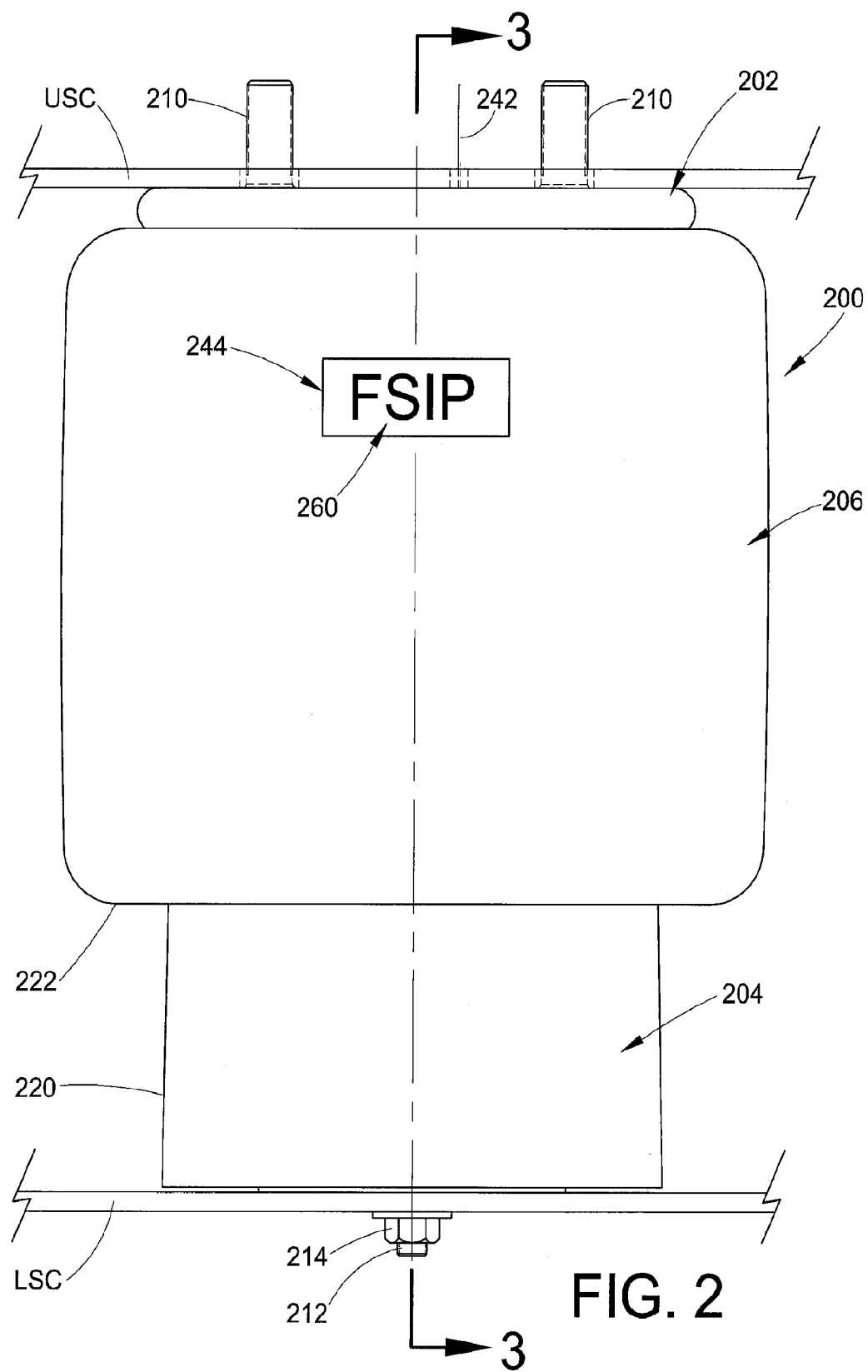
FIG. 2 is a side view of one example of a gas spring assembly in accordance with the subject matter of the present disclosure.
Figure 3:
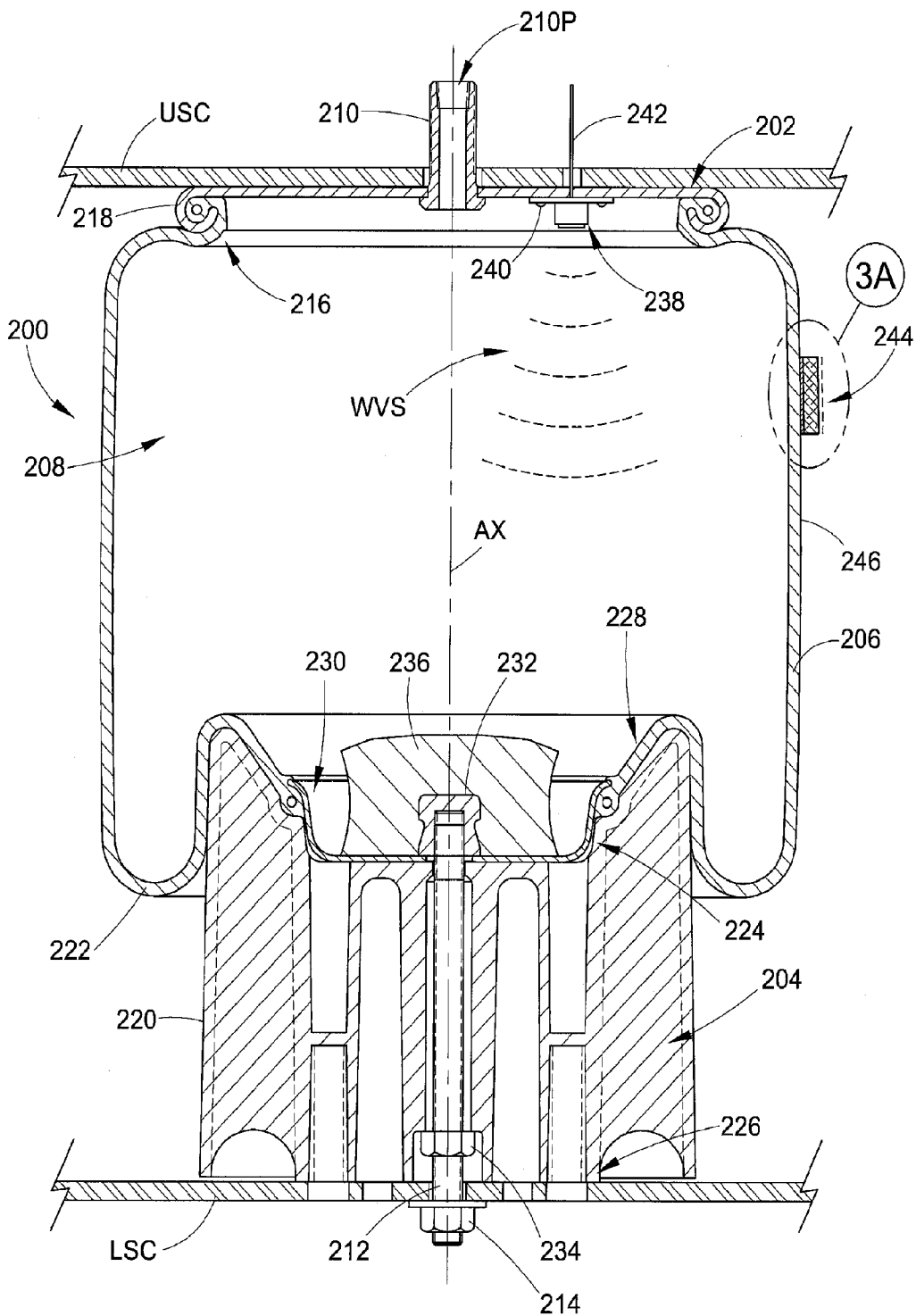
FIG. 3 is a side view, in partial cross-section, of the gas spring assembly in FIG. 2.
Figure 3A:
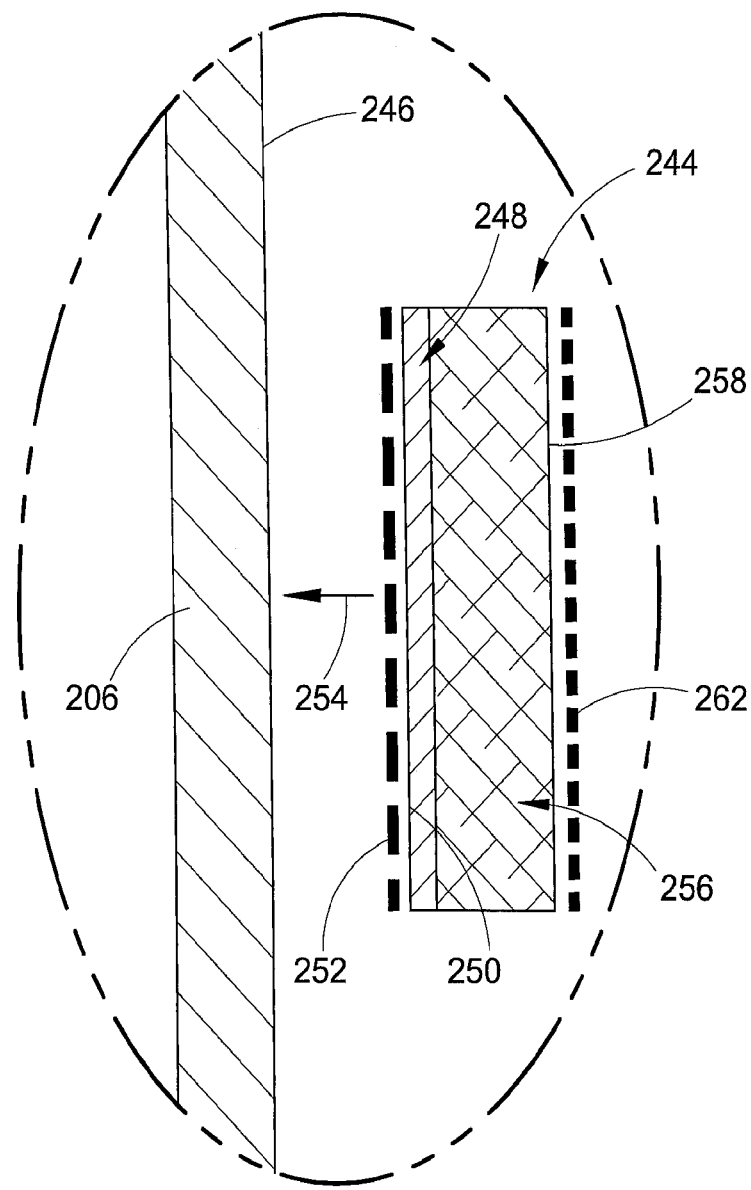
FIG. 3A is an enlarged view of the portion of the gas spring assembly in FIGS. 2 and 3 identified as Detail 3A in FIG. 3.

It will be appreciated that a component, device or assembly including an elastomeric article and a replacement indicator in accordance with the subject matter of the present disclosure can include an elastomeric article of any one of a wide variety of types, kinds and/or configurations. As one example, FIGS. 2, 3 and 3A illustrate a gas spring assembly 200 that includes an elastomeric article and can be representative of gas spring assemblies 102 of suspension system 100 in FIG. 1, for example. Gas spring assembly 200 includes a first end member 202, a second end member 204 that is spaced from the first end member, and an elastomeric article in the form of a flexible wall 206 that is secured between the first and second end members and at least partially defines a spring chamber 208 (FIG. 3) formed therebetween. Gas spring assembly 200 also includes a central axis AX (FIG. 3) extending longitudinally between the first and second end members.

Gas spring assembly 200 can be disposed between the associated sprung and unsprung masses of the associated vehicle in any suitable manner. For example, the first end member can be operatively connected to the associated sprung mass with the second end member disposed toward and operatively connected to the associated unsprung mass. In the embodiment shown in FIGS. 2 and 3, first end member 202 is secured along a first or upper structural component USC, such as associated vehicle body BDY in FIG. 1, for example, and can be secured thereon in any suitable manner, such as by using mounting studs 210, for example. A passage 210P (FIG. 3) can extend through one or more of the mounting studs in fluid communication with spring chamber 208, such as may be used for transferring pressurized gas into and/or out of the spring chamber, for example. Additionally, second end member 204 is secured along a second or lower structural component LSC, such as an axle AXL in FIG. 1, for example, in any suitable manner, such as by using a mounting stud 212 and a corresponding nut 214, for example.

First end member 202 and second end member 204 can be of any suitable type, kind, construction and/or configuration. In the exemplary embodiment shown in FIGS. 2 and 3, for example, first end member 202 is of a type commonly referred to as a bead plate that is secured to a first end 216 of flexible wall 206 using a crimped-edge connection 218. Additionally, second end member 204 is shown in the exemplary embodiment in FIGS. 2 and 3 as being of a type commonly referred to as a piston (or a roll-off piston) that has an outer side wall 220 that abuttingly engages flexible wall 206 such that a rolling lobe 222 is formed therealong. As gas spring assembly 200 is displaced between extended and collapsed conditions, rolling lobe 222 is displaced along outer side wall 220 in a conventional manner.

As identified in FIG. 3, second end member 204 extends generally between a first or upper end wall 224 and a second or lower end wall 226. A second end 228 of flexible wall 206 is secured on upper end wall 224 of second end member 204 using an end closure 230. The end closure can be secured on the second end member in any suitable manner. In the exemplary embodiment shown, a retaining nut 232 is threadably secured on mounting stud 212 and engages end closure 230. By securing mounting stud 212 on end member 204 using nut 234, the end closure can be drawn tight to upper end wall 224 to thereby secure second end 228 of the flexible wall therebetween. It is to be understood, however, that the arrangement shown and described is merely exemplary and that any other suitable construction and/or configuration can alternately be used. A jounce bumper 236 can, optionally, be supported within spring chamber 208, such as to inhibit direct contact between the first and second end member. It will be appreciated that the jounce bumper, if included, can be supported on or along an end member in any suitable manner. For example, jounce bumper 236 is shown as being received on and retained by retaining nut 232.

A height or distance sensing device 238 is shown in FIGS. 2 and 3 as being secured within spring chamber 208 along first end member 202 and being secured thereto using suitable fasteners 240. Height sensing device 238 can be of any suitable type, kind and/or construction, such as an ultrasonic sensor that transmits and receives ultrasonic waves WVS (FIG. 3), for example. Additionally, it will be appreciated that height sensing device 238 can be connected to other systems and/or components of a vehicle suspension system in any suitable manner. As shown in FIGS. 2 and 3, height sensing device 238 includes a lead or connection 242 that can be used for such communication purposes, such as is indicated by leads 124 of control system 118 in FIG. 1, for example.

A component, device or assembly in accordance with the subject matter of the present disclosure can have a replacement indicator operatively associated therewith in any suitable manner. In some cases, the replacement indicator can be secured on or along a rigid or non-elastomeric component (e.g., end member 202 and/or 204), such as along an exterior or outwardly exposed surface thereof, for example. In other cases, the replacement indicator may be secured on or along an elastomeric article (e.g., flexible wall 206) of the assembly (e.g., gas spring assembly 200), such as along an exterior or outwardly exposed surface thereof, for example. Additionally, in some cases, the replacement indicator can, optionally, be of a stiff or rigid construction relative to the comparatively flexible elastomeric article. In other cases, the replacement indicator can, optionally, include a backing or support element, such as, for example, may be used for mounting purposes or to provide additional stiffness to the replacement indicator. In still other cases, the replacement indicator can be of a flexible nature, such as, for example, may be suitable for conforming to an elastomeric article for mounting purposes and/or for flexing with the elastomeric article during dynamic operation and/or use thereof.

In the exemplary arrangements shown in FIGS. 1 and 2, for example, the replacement indicator is secured to the flexible wall of the gas spring assembly. That is, in FIG. 2, for example, a replacement indicator 244 is shown as being attached to an outer surface 246 of flexible wall 206, and can be secured thereto in any suitable manner. For example, in some cases, one or more mechanical fasteners may be used to secure a replacement indicator on an elastomeric article. Additionally, or in the alternative, a flowed-material joint (e.g., an adhesive) could be used, such as may be applied to either or both of the replacement indicator (e.g., replacement indicator 244) and the elastomeric article (e.g., flexible wall 206). In the arrangement shown in FIGS. 3 and 3A, for example, replacement indicator 244 includes an adhesive layer 248 disposed along a side 250 (FIG. 3A) of the replacement indicator.

In some cases, the replacement indicator and/or the elastomeric article can, optionally, include one or more protective layers, such as, for example, may be useful for preventing inadvertent adhesion of the replacement indicator to an object and/or for minimizing exposure of the replacement indicator to one or more environmental agents prior to use. As identified in FIG. 3A, for example, replacement indicator 244 is shown as including a protective layer 252 disposed along side 250, and suitable for at least partially covering or otherwise protecting adhesive layer 248 from inadvertent adhesion prior to use. Protective layer 252 is removable (e.g., by peeling) such that the adhesive layer can be exposed immediately prior to securement, as is indicated by arrow 254 in FIG. 3A.

A replacement indicator in accordance with the subject matter of the present disclosure will also include an element, a section, or a portion of material that is suitable for providing a visual indication upon undergoing exposure a predetermined level of one or more environmental agents. It will be appreciated that any suitable visual indication can be used, such as, for example, a simple change in the color of at least a portion of the element from one color to another color. In the exemplary arrangement shown in FIGS. 3 and 3A, replacement indicator 244 is shown as including a layer of material 256 at least a portion of which is capable of undergoing a color change upon exposure to a predetermined level of one or more environmental agents, such as may be visually apparent from along a side 258 of the replacement indicator. In some cases, the change in color could be presented in a pattern (e.g., in the form of one or more symbols and/or characters), as is represented in FIG. 2 by characters 260, for example. Additionally, replacement indicator 244 is shown as, optionally, including a protective layer 262 that extends at least partially across or otherwise at least partially covers side 258 of the replacement indicator.

Another example of an assembly in accordance with the subject matter of the present disclosure that includes an elastomeric article and a replacement indicator operatively associated with the elastomeric article that is capable of providing a visual indication of the exposure of the elastomeric article to a predetermined level of one or more environmental agents is shown in FIGS. 4-6A as a gas spring assembly 300, such as may be supported between upper structural component USC (FIGS. 2 and 3) and lower structural component LSC (FIGS. 2 and 3). As noted above, it will be appreciated that the upper and lower structural components are merely representative of structural components of any suitable type, kind and/or configuration, such as body BDY and axle AXL of vehicle VHC in FIG. 1, for example.

Gas spring assembly 300 is shown as including an end member 302, such as a bead plate, for example, and an end member 304, such as a bead plate, for example, that is spaced from end member 302. An elastomeric article in the form of a flexible wall 306 is secured between the end members and at least partially forms a spring chamber 308 therebetween. Gas spring assembly 300 also includes a central axis AX (FIG. 6) extending longitudinally between the end members.

Gas spring assembly 300 is shown as being of a type commonly referred to as a convoluted or bellows-type construction. As such, the flexible wall of the gas spring assembly can have any suitable number of one or more convoluted wall portions disposed between the opposing end members. In the exemplary embodiment shown in FIGS. 4-6A, flexible wall 306 includes a girdle hoop 310 (FIG. 6) disposed approximately midway along the flexible wall. A convoluted wall portion 312 extends between the girdle hoop and end member 302, and a convoluted wall portion 314 extends between the girdle hoop and end member 304.

It will be appreciated that gas spring assembly 300 can be of any type or kind of convoluted spring construction. For example, end members 302 and 304 can be secured on opposing open ends 316 and 318 of flexible wall 306 such that a substantially fluid-tight seal is formed therebetween. In the arrangement shown, an outer peripheral edge of the end members is crimped or otherwise deformed about a portion of the end of the flexible wall, as is indicated by curved outer wall portions 320 and 322. A connection 324 can be provided on or along one of the end members (e.g., end member 302) such as may be used for attachment of a gas transmission line (e.g., gas transmission line 116 in FIG. 1) and can include a passage 326 extending therethrough in fluid communication with spring chamber 308, such as may be used for transferring pressurized gas into and/or out of the spring chamber, for example. The gas spring assembly can also include any suitable number of one or more securement features, such as mounting studs 328 and/or threaded passages (not shown), for example.

Gas spring assembly 300 also includes one or more replacement indicators that can be operatively secured on or along one or more non-elastomeric components and/or one or more elastomeric articles of the gas spring assembly. In the exemplary arrangement shown in FIGS. 4-6, a replacement indicator 330 is shown as being disposed on or along a non-elastomeric component (e.g., end member 302). Additionally, or in the alternative, a replacement indicator 332 (FIG. 5) can be disposed on or along an elastomeric article (e.g., flexible wall 306). In some cases, replacement indicator 332 can be substantially similar to replacement indicator 244 described above in connection with FIGS. 2, 3 and 3A, and can be secured on or along flexible wall 306 in a manner substantially similar to that discussed above in connection with the securement of replacement indicator 244 to flexible wall 206. It will be appreciated, however, that other arrangements could alternately be used.

As discussed above, it will be appreciated that a replacement indicator in accordance with the subject matter of the present disclosure can take any suitable configuration and/or construction. As identified in FIG. 6A, replacement indicator 330 includes a backing member or support plate 334 disposed along a side 336 of the replacement indicator. Replacement indicator 330 also includes an element, a section, or a portion of material that is suitable for providing a visual indication upon undergoing exposure a predetermined level of one or more environmental agents, as is represented in FIGS. 4-6A by an indicator layer 338 disposed along side 340 of the replacement indicator.

Figure 6:
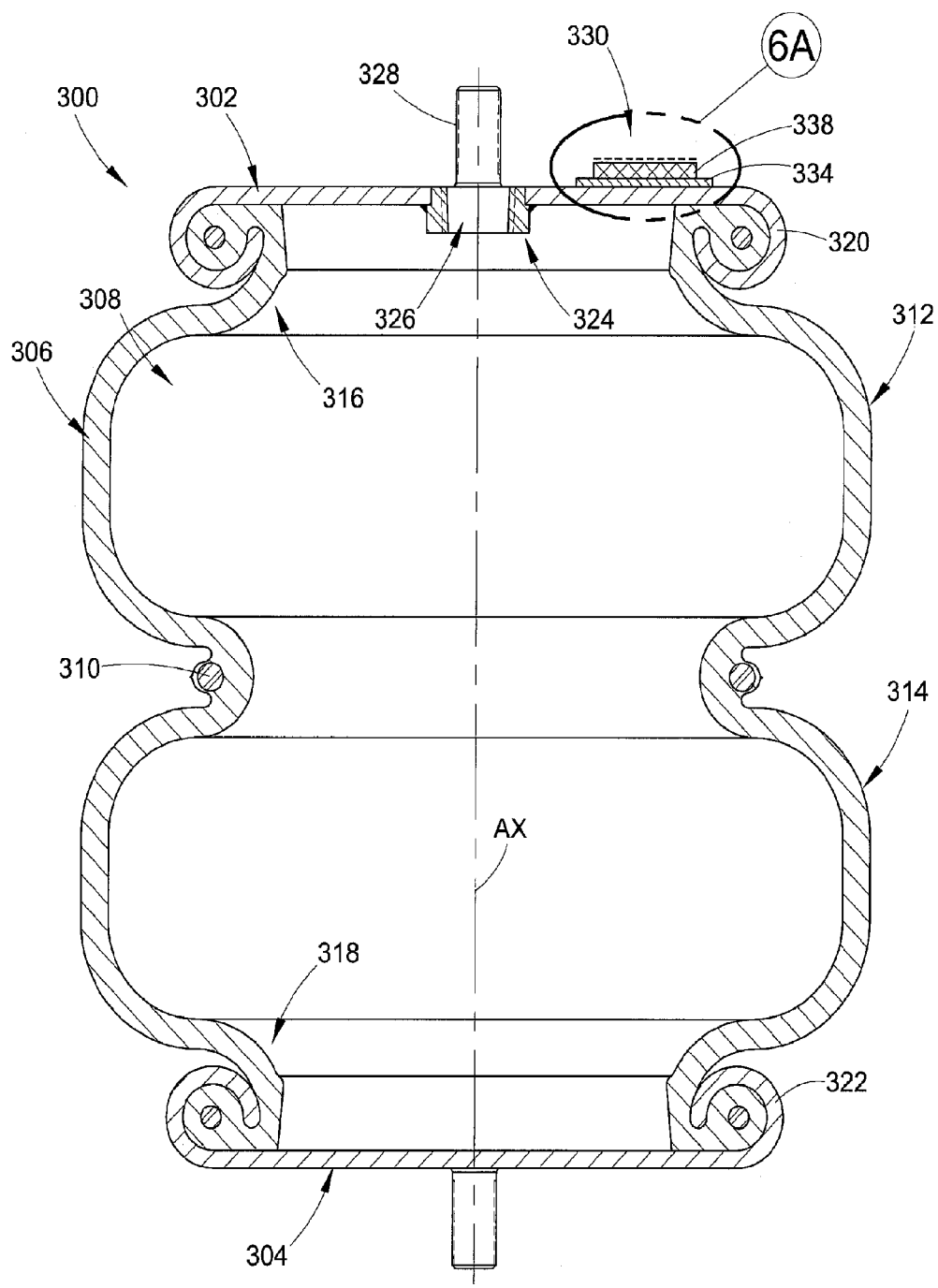
FIG. 6 is a side view, in partial cross-section, of the gas spring assembly in FIGS. 4 and 5.
Figure 6A:
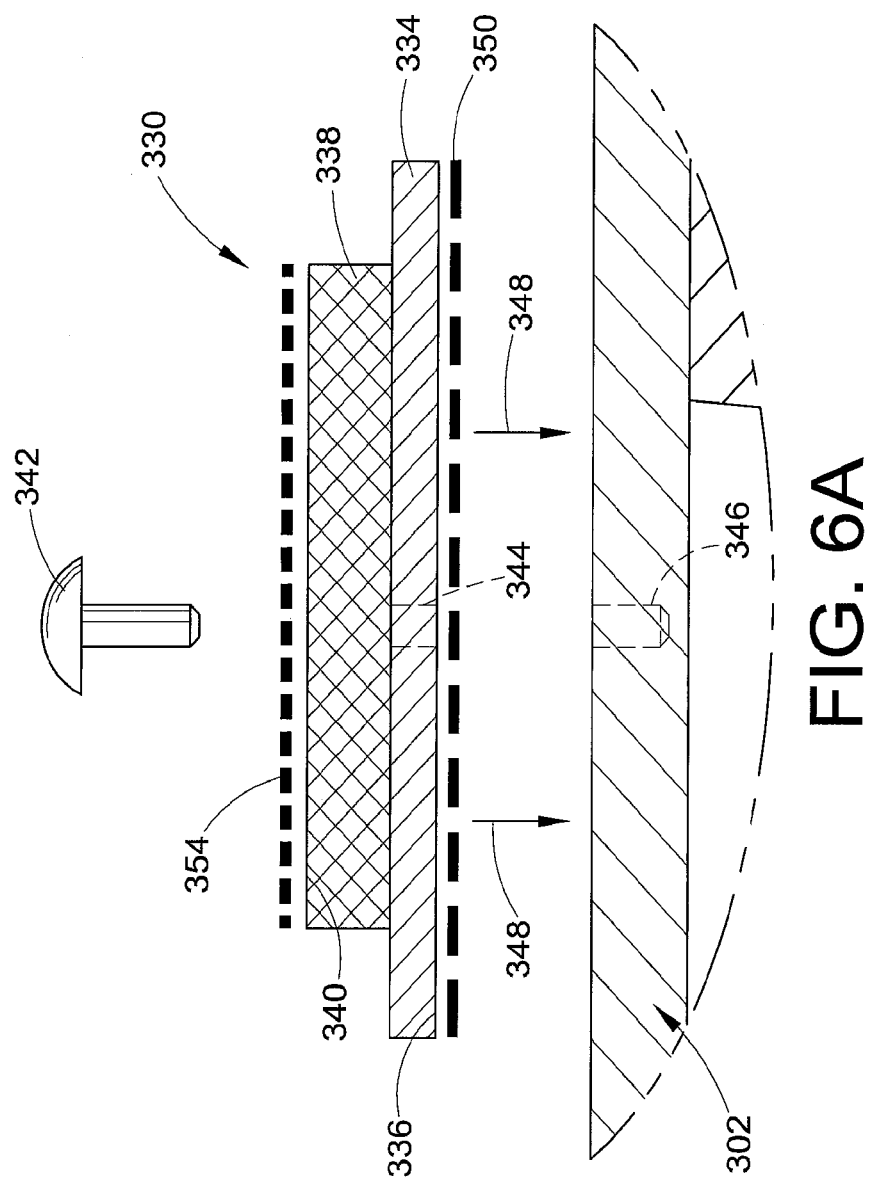
FIG. 6A is an enlarged view of the portion of the gas spring assembly in FIGS. 4-6 identified as Detail 6A in FIG. 6.

Replacement indicator 330 can be secured on or along the non-elastomeric component (e.g., end member 302) in any suitable manner. For example, one or more mechanical fasteners could be used to secure the replacement indicator on the non-elastomeric component. As illustrated in FIG. 6A, for example, a plurality of fasteners 342 are shown securing replacement indicator 330 along end member 302. In some cases, fasteners 342 can take the form of drive screws or threaded fasteners can extend through passages 344 in support plate 334 and into engagement with passages 346 in end member 302. In this manner, the replacement indicator can be positioned in abutting engagement along the non-elastomeric component (e.g., end member 302) and secured thereto, as is represented by arrows 348. It will be appreciated, however, that other arrangements could alternately be used.

Additionally, or in the alternative, a flowed-material joint could be used to secure the replacement indicator on or along the non-elastomeric component, such as by applying an adhesive material to either or both of the replacement indicator (e.g., replacement indicator 330) and the non-elastomeric component (e.g., end member 302). In the arrangement shown in FIG. 6A, for example, replacement indicator 330 can, optionally, include an adhesive layer 350 disposed along a side 336 of the replacement indicator.

Figure 4:
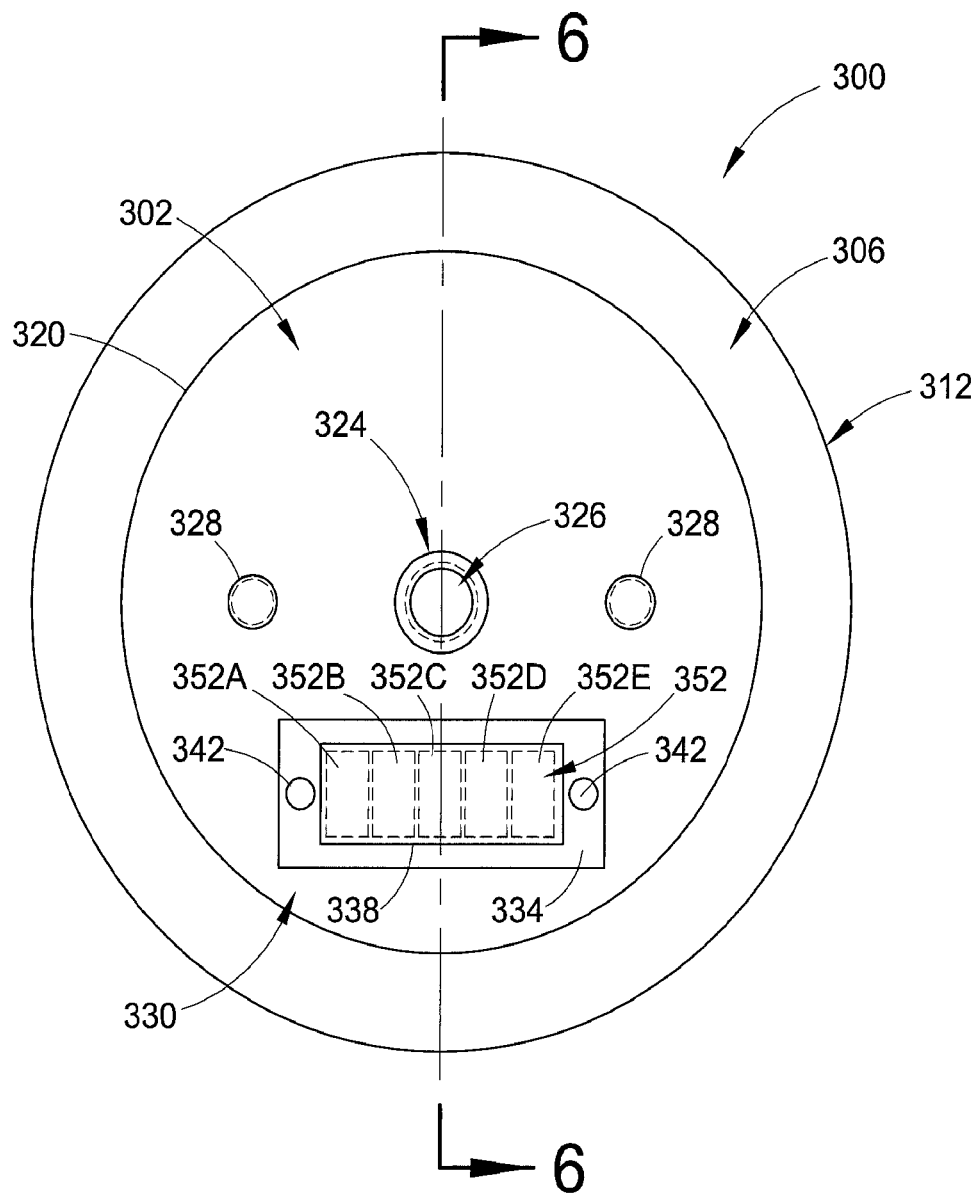
FIG. 4 is a top plan view of another example of a gas spring assembly in accordance with the subject matter of the present disclosure.
Figure 5:
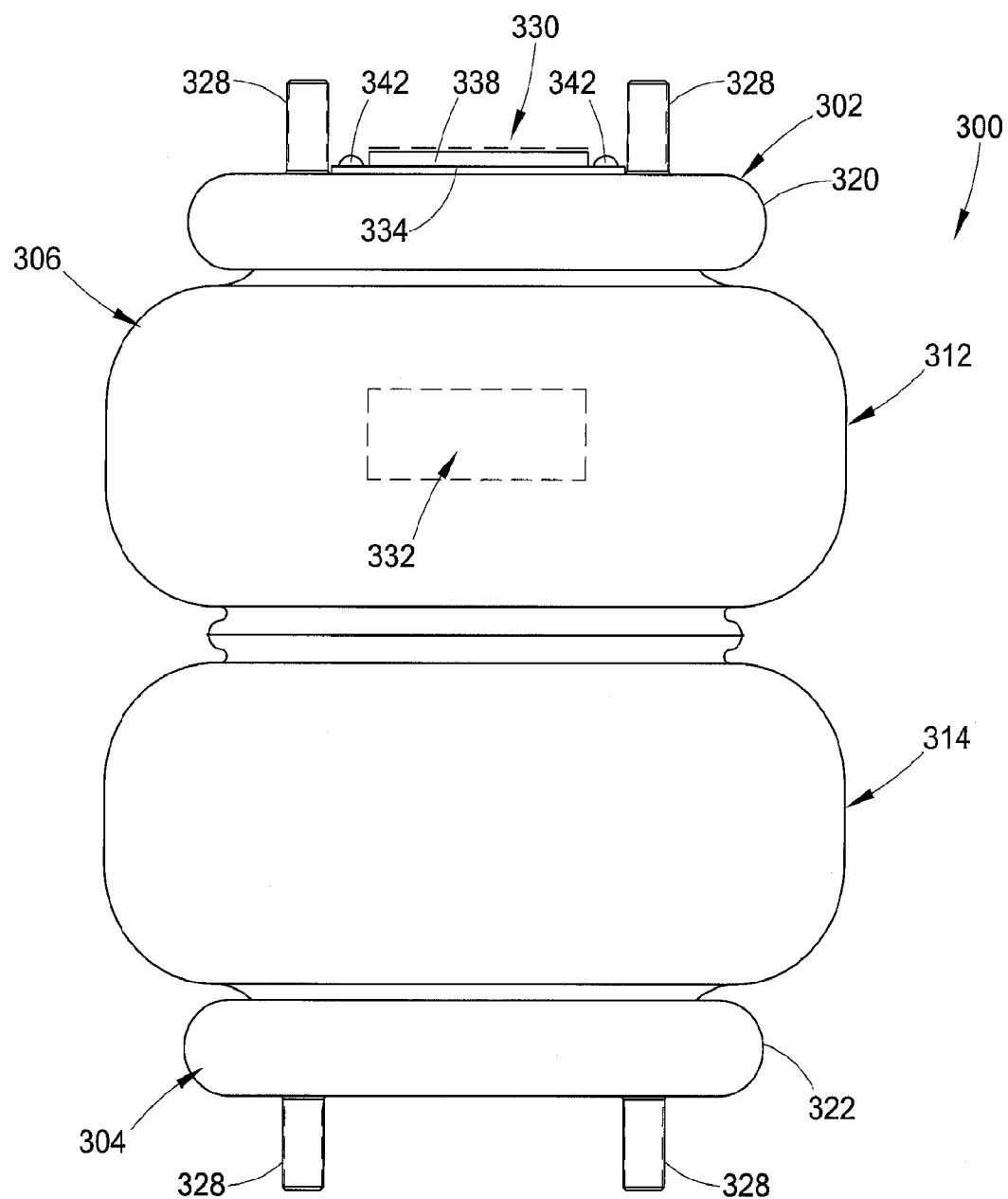
FIG. 5 is a side view of the gas spring assembly in FIG. 4.

As discussed above, replacement indicator 330 is operative to provide a visual indication upon undergoing exposure a predetermined level of one or more environmental agents. It will be appreciated that any suitable visual indication can be used, such as, for example, a simple change in the color of at least a portion of the element from one color to another color. In some cases, a plurality of color change identifiers could be included, as is represented in FIG. 4 by boxes 352, for example. In some cases, each of the plurality of color change identifiers could be capable of withstanding a different predetermined level of one or more environmental agents before undergoing a change in color. As one example, box 352A could be capable of withstanding a first predetermined level and box 352E could be capable of withstanding a fifth predetermined level that is greater than the first predetermined level. In such case, boxes 352B-D could be capable of withstanding increasing predetermined levels such that the replacement indicator can provide a visual representation of the cumulative level of one or more environmental agents to which the replacement indicator has been exposed.

In some cases, the replacement indicator and/or the elastomeric article can, optionally, include one or more protective layers, such as, for example, may be useful for preventing inadvertent adhesion of the replacement indicator to an object and/or for minimizing exposure of the replacement indicator to one or more environmental agents prior to use. As identified in FIG. 6A, for example, replacement indicator 330 is shown as including a protective layer 354 disposed along side 340, and suitable for at least partially covering or otherwise protecting indicator layer 338 to minimizing exposure of the replacement indicator to one or more environmental agents prior to use. Protective layer 354 and/or a protective layer (not shown) that may be disposed along adhesive layer 350 are preferably removable (e.g., by peeling) such that the indicator layer and/or adhesive layer can be exposed immediately prior to use.

Figure 7:
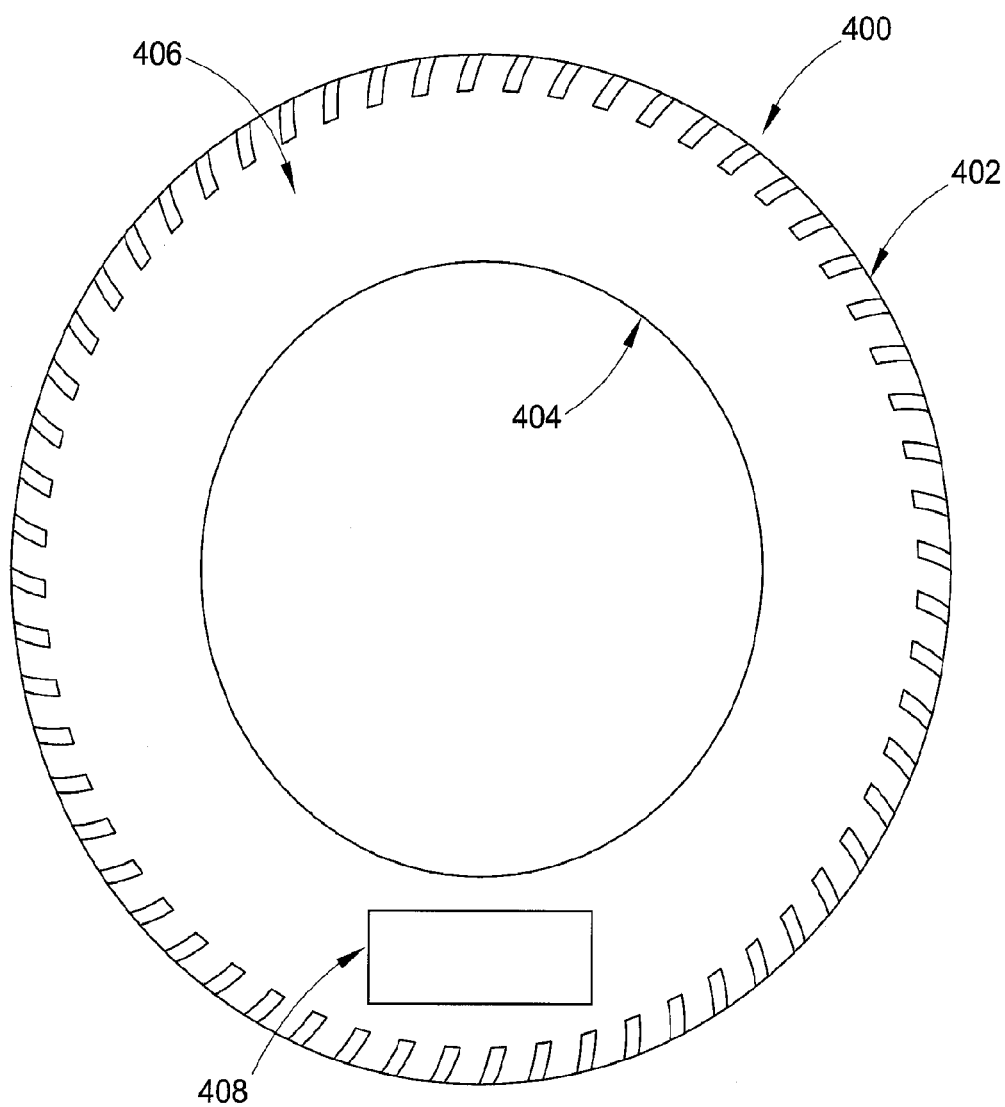
FIG. 7 is a side view of a pneumatic tire in accordance with the subject matter of the present disclosure.

A further example of an assembly in accordance with the subject matter of the present disclosure that includes an elastomeric article and a replacement indicator operatively associated with the elastomeric article that is capable of providing a visual indication of the exposure of the elastomeric article to a predetermined level of one or more environmental agents is shown in FIG. 7 as a pneumatic tire 400, and can be representative of wheels WHL of vehicle VHC in FIG. 1, for example. Pneumatic tire 400 is shown as including a tread portion 402 dispose along the outer periphery of the pneumatic tire. Bead portions 404 (only one of which is shown) are disposed radially-inwardly from tread portion 402, and are dimensioned for mounting the pneumatic tire on a rim or wheel. Pneumatic tire 400 is also shown as including side wall portions 406 (only one of which is shown) that extend radially between and interconnect tread portion 402 and bead portions 404.

A replacement indicator 408 is secured to side wall portion 406 of the tire. It will be appreciated that replacement indicator 408 can include any combination of the one or more of the features and/or details discussed above in connection with replacement indicators 126, 244, 330 and/or 332. As such, a detailed description of such features is not repeated here. Additionally, it will be appreciated that any suitable method or arrangement can be used for securement of replacement indicator 408 on or along pneumatic tire 400, such as have been discussed above in detail in connection with replacement indicators 126, 244, 330 and/or 332. As such, it will be understood that the foregoing discussion of the features and details of and relating to replacement indicators 126, 244, 330 and/or 332 are equally applicable to replacement indicator 408 and can be likewise directed thereto.

Furthermore, it will be appreciated that replacement indicators 126, 244, 330 and 332 may be configured to indicate time for replacement after exposure to the same or different predetermined levels of one or more of the same or different environmental agent(s). It will be appreciated that any suitable durations or ranges of time periods can be used, such as cumulative exposure over a duration within a range of from about 1 month to about 72 months, for example. In some cases, threshold exposure levels could be used in addition to, or as an alternative to, cumulative exposure levels. Also, though the replacement indicators are depicted as being positioned at specific locations in the drawing figures, it should be understood that such locations are merely exemplary and that any other suitable location could alternately be used.

Figure 8:
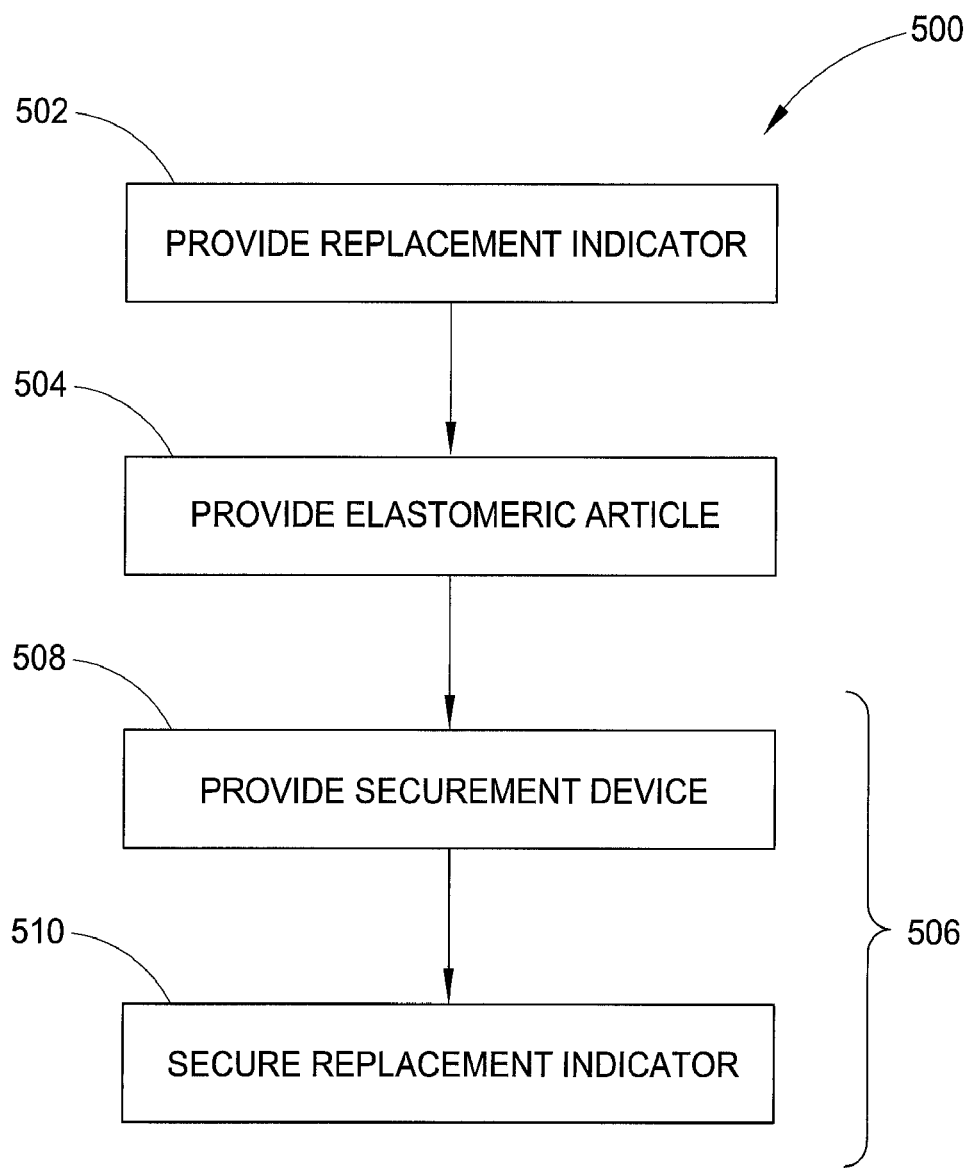
FIG. 8 is graphical representation of one example of a method of manufacturing an elastomeric article in accordance with the subject matter of the present disclosure.

FIG. 8 is a graphical representation of one example of a method 500 of manufacturing an assembly in accordance with the subject matter of the present disclosure, such as one of gas spring assemblies 102, 200 and 300 and/or pneumatic tire 400, for example. Method 500 includes providing a replacement indicator (e.g., replacement indicator 126, 244, 330 and/or 332) that includes a color change material capable of changing color upon exposure to a predetermined level of one or more environmental agents, as is represented by item number 502 in FIG. 8. Method 500 also includes providing an elastomeric article (e.g., flexible wall 206 and 306, side wall portion 406 of pneumatic tire 400), as is represented by item number 504 in FIG. 8. Method 500 can further include supporting the replacement indicator in operative association with the elastomeric article such that exposure to one or more environmental agents is approximately equal for the replacement indicator and the elastomeric article, such as is represented by item number 506 in FIG. 8. In some cases, method 500 can include providing a securement feature or device (e.g., adhesive layer 252, adhesive layer 350 and/or fasteners 342), as is represented in FIG. 8 by item number 508. Additionally, method 500 can include securing the replacement indicator (e.g., replacement indicator 126, 244, 330 and/or 332) on one of a non-elastomeric component (e.g., end member 202, 204, 302 and/or 304) and an elastomeric article (e.g., flexible wall 206, 306 and/or side wall portion 406) using the securement feature and/or device, as is represented in FIG. 8 by item number 510.

Figure 9:
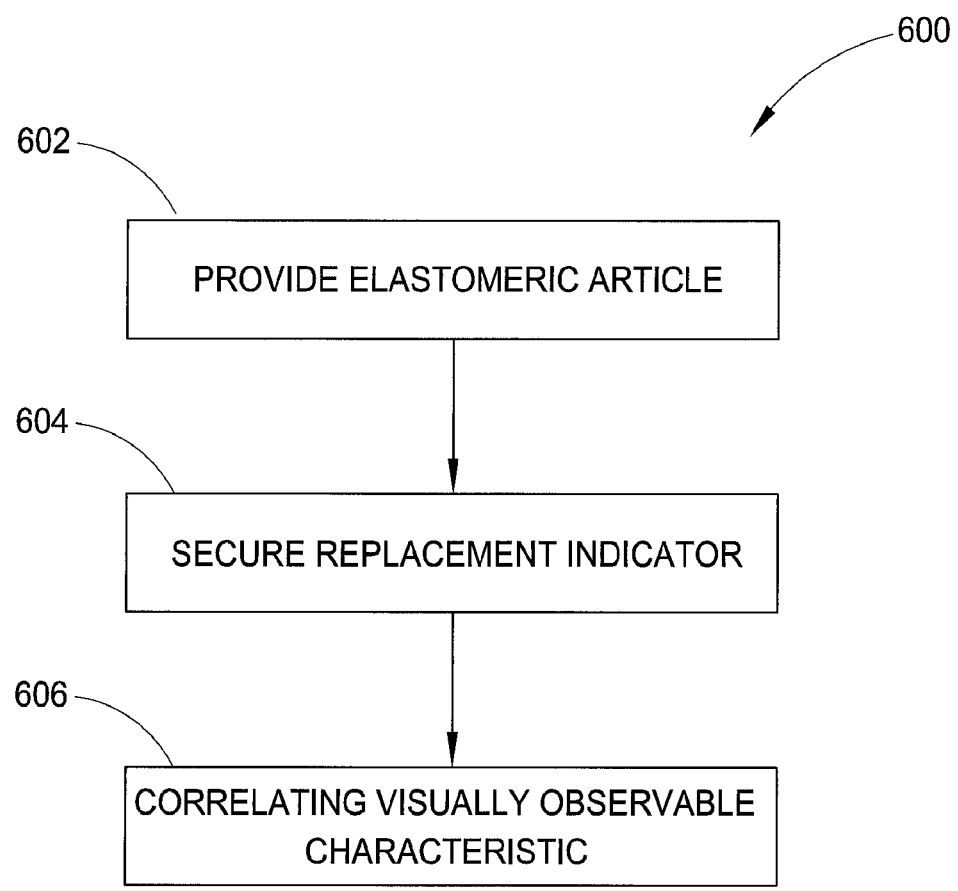
FIG. 9 is graphical representation of one example of a method of monitoring a characteristic of an elastomeric article in accordance with the subject matter of the present disclosure.

FIG. 9 is a graphical representation of one example of a method 600 of monitoring a characteristic of an elastomeric article in accordance with the subject matter of the present disclosure. Method 600 includes providing an elastomeric article (e.g., flexible wall 206 and 306, side wall portion 406 of pneumatic tire 400) to be monitored, as is represented by item number 602 in FIG. 9. Method 600 also include providing a replacement indicator (e.g., replacement indicator 126, 244, 330 and/or 332) that includes a color change material capable of changing color upon exposure to a predetermined level of one or more environmental agents, as is represented by item number 604 in FIG. 9. Method 600 further includes correlating one or more visually-observable characteristics (e.g., colors of the color change material) with one or more corresponding characteristics of the elastomeric article, as is represented by item number 606 in FIG. 9, such that a characteristic of the elastomeric article can be identified by the approximate color of the replacement indicator upon exposure of the replacement indicator and the elastomeric article to a predetermined level of the one or more environmental agents. As an example, one or more colors of the color change material (e.g., indicator layer 256, 338) can be correlated with a mechanical property (e.g., fatigue life) of the elastomeric article.

A replacement indicator in accordance with the subject matter of the present disclosure can include an element, section or portion of material, which may be collectively referred to herein as an indicator layer, that is capable of providing a visual indication of the exposure of the element, section or portion of material to a predetermined level of one or more environmental agents. In some cases, the indicator layer can include material that changes color upon exposure to a predetermined level of one or more environmental agents. In other cases, the indicator layer can include material that changes other visual characteristics, such as a change from one pattern to another pattern and/or from one or more characters or symbols to one or more other, different characters or symbols. In still other cases, a combination of such visually-observable changes could be used. Additionally, in some cases, the predetermined level of exposure may be a predetermined, cumulative level of exposure that occurs over an extended period of time. In other cases, the predetermined level of exposure could be a maximum or threshold level that occurs at a particular point in time or over a short duration.

As one example, the material of the indicator layer can include a color change material in that includes an antioxidant and/or an antiozonant. In some cases, the antioxidant may exhibit color change in response to heat exposure. In some cases, heat exposure may be measured based on any suitable combination of duration and temperature to which an indicator may be exposed. For example, the indicator may change after exposure to a temperature at or above a predetermined level for a predetermined time. Additionally, or in the alternative, the antiozonant may exhibit color change in response to ozone exposure. In some cases, the replacement indicator can further include a color static material. In such cases, the color static material may have a higher affinity for the one or more environmental agents than the color change material. As a result, the color static material may be consumed or otherwise used up during a period of exposure to the environmental agents (e.g., ozone). In such a system, the color change material may not exhibit any color change until a first amount of the color static material is consumed. Thus, a predetermined level of exposure may be set by the amount of the color static material included in the replacement indicator. The first amount may be the entirety or near the entirety of the color static material or any partial amount thereof.

Additionally, or in the alternative, the indicator layer could include an outer indicator sublayer and an inner indicator sublayer. In some cases, the outer indicator sublayer can include or otherwise present a first visual pattern or appearance (e.g., a solid colored panel, a geometric pattern or one or more characters and/or symbols) and the inner indicator sublayer can include or otherwise present a second visual pattern or appearance (e.g., a non-solid colored panel, a different geometric pattern or one or more different characters and/or symbols). In use, the outer indicator sublayer can wear away or be otherwise consumed or used up upon exposure to a predetermined level of one or more environmental agents (e.g. by including a compound which reacts with the environmental agent(s) in the outer sublayer). As a result, the second pattern may not be visible when the outer indicator sublayer is in place but may become visible as the outer indicator sublayer wears away or is otherwise consumed. The change from the first visual pattern to the second visual pattern can indicate that a predetermined level of exposure to the one or more environmental agent(s) has been reached. It will be appreciated that the outer indicator sublayer can cover all or only a portion of the inner indicator sublayer.

The indicator layer can also include multiple outer indicator sublayers, with one or more of the outer indicator sublayers including a different visual pattern or other visually-observable characteristic. In such case, each of the different visual patterns or other observable characteristics can provide an approximate indication of the level of exposure and, thus, can be correlated or otherwise used to approximate the remaining useful life of the elastomeric article. For example, each of the different visual patterns or other visually-observable characteristics can display or otherwise represent a number of years, months, weeks, or days until the elastomeric article should be replaced.

As used herein with reference to certain features, elements, components and/or structures, numerical ordinals (e.g., first, second, third, fourth, etc.) may be used to denote different singles of a plurality or otherwise identify certain features, elements, components and/or structures, and do not imply any order or sequence unless specifically defined by the claim language. Additionally, the terms "transverse," and the like, are to be broadly interpreted. As such, the terms "transverse," and the like, can include a wide range of relative angular orientations that include, but are not limited to, an approximately perpendicular angular orientation.

Furthermore, the phrase "flowed-material joint" and the like are to be interpreted to include any joint or connection in which a liquid or otherwise flowable material (e.g., a melted metal or combination of melted metals) is deposited or otherwise presented between adjacent component parts and operative to form a fixed and substantially fluid-tight connection therebetween. Examples of processes that can be used to form such a flowed-material joint include, without limitation, welding processes, brazing processes and soldering processes. In such cases, one or more metal materials and/or alloys can be used to form such a flowed-material joint, in addition to any material from the component parts themselves. Another example of a process that can be used to form a flowed-material joint includes applying, depositing or otherwise presenting an adhesive between adjacent component parts that is operative to form a fixed and substantially fluid-tight connection therebetween. In such case, it will be appreciated that any suitable adhesive material or combination of materials can be used, such as one-part and/or two-part epoxies, for example.

Further still, terms such as "gas," "pneumatic" and "fluid" as well as variants thereof, are used herein to broadly refer to and include any gaseous or vaporous fluid. Most commonly, air is used as the working medium of gas spring devices, such as those described herein, as well as suspension systems and other components thereof. However, it will be understood that any suitable gaseous fluid could alternately be used.

It will be recognized that numerous different features and/or components are presented in the embodiments shown and described herein, and that no one embodiment is specifically shown and described as including all such features and components. However, it is to be understood that the subject matter of the present disclosure is intended to encompass any and all combinations of the different features and components that are shown and described herein, and, without limitation, that any suitable arrangement of features and components, in any combination, can be used. Thus it is to be distinctly understood claims directed to any such combination of features and/or components, whether or not specifically embodied herein, are intended to find support in the present disclosure.

Thus, while the subject matter of the present disclosure has been described with reference to the foregoing embodiments and considerable emphasis has been placed herein on the structures and structural interrelationships between the component parts of the embodiments disclosed, it will be appreciated that other embodiments can be made and that many changes can be made in the embodiments illustrated and described without departing from the principles hereof. Obviously, modifications and alterations will occur to others upon reading and understanding the preceding detailed description. Accordingly, it is to be distinctly understood that the foregoing descriptive matter is to be interpreted merely as illustrative of the subject matter of the present disclosure and not as a limitation. As such, it is intended that the subject matter of the present disclosure be construed as including all such modifications and alterations insofar as they come within the scope of the appended claims and any equivalents thereof.

The invention claimed is:

1. A replacement indicator for use in cooperation with an associated elastomeric spring member having an associated exterior surface, said replacement indicator comprising a layer of material including a first side securable along the associated exterior surface of the associated elastomeric spring member and a second side facing opposite said first side such that said second side is exposable to one or more environmental agents to which the associated elastomeric spring member would be simultaneously exposed in an installed condition of said replacement indicator, said layer of material having a visually-observable characteristic that changes from a first color to a second color that is different from said first color upon exposure to a predetermined level of said one or more environmental agents with said change from said first color to said second color capable of being correlated to a change in a material characteristic of the associated elastomeric spring member.

2. A replacement indicator according to claim 1, wherein said one or more environmental agents includes ozone ($O_3$).

3. A replacement indicator according to claim 1, wherein said one or more environmental agents includes oxygen ($O_2$).

4. A replacement indicator according to claim 1, wherein said one or more environmental agents includes heat.

5. A replacement indicator according to claim 1 further comprising an adhesive layer disposed along said first side of said layer of material and adapted to attach said replacement indicator to the associated exterior surface of the associated elastomeric spring member.

6. A replacement indicator according to claim 5 further comprising a removable protective layer extending across at least a portion of said adhesive layer such that said protective layer can at least partially inhibit inadvertent adhesion of said adhesive layer to an object prior to use.

7. A replacement indicator according to claim 1 further comprising a protective layer disposed along at least a portion of said second side of said layer of material and extending across at least a portion of said layer of material such that said protective layer can at least partially inhibit exposure of said layer of material to said one or more environmental agents prior to use.

8. A replacement indicator according to claim 1, wherein said change of said visually-observable characteristic from said first color to said second color is presented as at least one of a pattern, one or more symbols and one or more characters in said layer of material having said visually-observable characteristic.

9. A replacement indicator according to claim 1, wherein said layer of material is a color change material that includes at least one of an antioxidant and an antiozonant.

10. A replacement indicator according to claim 9, wherein said layer of material includes a color static material that has a higher affinity for said one or more environmental agents than said color change material.

11. A method of manufacturing an assembly, said method comprising:
providing a replacement indicator according to claim 1;
providing an elastomeric spring member; and,
attaching said replacement indicator to said elastomeric spring member.

12. A method according to claim 11, wherein said replacement indicator includes a removable protective layer; and, said method further comprises one of:
removing said removable protective layer prior to attaching said replacement indicator to said elastomeric spring member; and,
removing said removable protective layer after attaching said replacement indicator to said elastomeric spring member.

13. A method of monitoring a characteristic of an elastomeric spring member, said method comprising:
providing an elastomeric spring member to be monitored;
providing a replacement indicator according to claim 1; and,
correlating one or more visually-observable characteristics of said layer of material with one or more material characteristics of said elastomeric spring member, such that a material characteristic of said elastomeric spring member can be identified by said change in said visually-observable characteristic of said replacement indicator upon exposure of said replacement indicator and said elastomeric spring member to a common, predetermined level of said one or more environmental agents.

14. A replacement indicator according to claim 1, wherein said layer of material is a first layer of material having a first visually-observable characteristic, and said replacement indicator further comprises a second layer of material disposed laterally adjacent said first layer of material, said second layer of material including a first side securable along the associated exterior surface of the associated elastomeric spring member and a second side facing opposite said first side such that said second side is exposable to one or more environmental agents to which the associated elastomeric spring member would be simultaneously exposed in an installed condition of said replacement indicator, said second layer of material having a second visually-observable characteristic that changes from said first color to said second color upon exposure to a second predetermined level of said one or more environmental agents.

15. A replacement indicator according to claim 14 further comprising a backing member including a first side securable along the associated exterior surface of the associated elastomeric spring member and a second side facing opposite said first side with said first and second layers of material secured to said backing member along said second side thereof.

16. An assembly comprising:
a gas spring assembly including:
a first end member;
a second end member spaced from said first end member such that a longitudinal axis extends therebetween; and,
a flexible wall extending circumferentially about said longitudinal axis and longitudinally between opposing first and second ends, said flexible wall including an interior surface and an exterior surface with said first end member secured across said first end of said flexible wall and said second end member secured across said second end of said flexible wall such that a spring chamber is at least partially formed by said interior surface of said flexible wall between said first and second end members; and,
a replacement indicator operatively associated with said as spring assembly, said replacement indicator including:
a first layer of material including a first side oriented toward said gas spring assembly and a second side facing opposite said first side with said second side being exposed to one or more environmental agents, said first layer of material having a first visually-observable characteristic that changes from one color to another color upon exposure to a first predetermined level of said one or more environmental agents such that said change in said visually-observable characteristic can be correlated to a first level of exposure of said material characteristic of said flexible wall to said one or more environmental agents; and,
a second layer of material disposed laterally adjacent said first layer of material, said second layer of material including a first side oriented toward said gas spring assembly and a second side facing opposite said first side with said second side being exposed to said one or more environmental agents, said second layer of material having a second visually-observable characteristic that changes from one color to another color upon exposure to a second predetermined level of said one or more environmental agents such that said change in said visually-observable characteristic can be correlated to a second level of exposure of said material characteristic of said flexible wall to said one or more environmental agents.

17. An assembly according to claim 16, wherein said replacement indicator is attached to said flexible wall.

18. An assembly according to claim 16, wherein said replacement indicator is attached to said first end member.

19. An assembly according to claim 16 further comprising a backing member including a first side securable along said gas spring assembly and a second side facing opposite said first side with said first and second layers of material secured to said backing member along said second side thereof.

20. A replacement indicator for use in cooperation with an associated elastomeric spring member, said replacement indicator comprising:
a layer of material including a first side secured along an exterior surface of said elastomeric spring member and a second side opposing said first side with said second side being exposed to one or more environmental agents, said layer of material having a visually-observable characteristic that changes from a first color to a second color that is different from said first color upon exposure to a predetermined level of said one or more environmental agents with said change from said first color to said second color capable of being correlated to a change in a material characteristic of the associated elastomeric spring;

an adhesive layer disposed on said first side of said layer of material;

a first removable protective layer extending across at least a portion of said adhesive layer such that said first removable protective layer can at least partially inhibit inadvertent adhesion of said adhesive layer to an object prior to use; and, a second removable protective layer disposed on said second side of said layer of material and extending across at least a portion of said layer of material such that said protective layer can at least partially inhibit exposure of said layer of material to said one or more environmental agents prior to use.

* * * * *

UNITED STATES PATENT AND TRADEMARK OFFICE
CERTIFICATE OF CORRECTION

PATENT NO. : 9,588,053 B2
APPLICATION NO. : 14/379668
DATED : March 7, 2017
INVENTOR(S) : Neiten et al.

Page 1 of 1

It is certified that error appears in the above-identified patent and that said Letters Patent is hereby corrected as shown below:

In the Claims

In Column 16, Line 15, delete "as" and insert -- gas --.

Signed and Sealed this
Eighth Day of August, 2017

Joseph Matal
*Performing the Functions and Duties of the*
*Under Secretary of Commerce for Intellectual Property and*
*Director of the United States Patent and Trademark Office*